United States Patent [19]

Coulston et al.

[11] Patent Number: 4,663,346
[45] Date of Patent: May 5, 1987

[54] INSECT REPELLENT

[75] Inventors: Frederick Coulston, Rensselaer, N.Y.; Friedrich W. A. G. K. Korte, Attenkirchen, Fed. Rep. of Germany

[73] Assignee: Angus Chemical Company, Northbrook, Ill.

[21] Appl. No.: 615,522

[22] Filed: May 30, 1984

[51] Int. Cl.$^4$ .............................................. A01N 43/16
[52] U.S. Cl. .................... 514/456; 514/919; 424/DIG. 10
[58] Field of Search ...................... 424/279, DIG. 10; 514/919, 456

[56] References Cited

U.S. PATENT DOCUMENTS

| Re. 29,829 | 11/1978 | Bordenca et al. | 424/325 |
|---|---|---|---|
| 1,995,247 | 3/1935 | Haring | 424/281 |
| 3,089,877 | 5/1963 | Korte et al. | 424/279 |
| 4,414,227 | 11/1983 | Tomlinson, Sr. et al. | 424/331 |
| 4,416,881 | 11/1983 | McGovern et al. | 424/248 |
| 4,419,360 | 12/1983 | Smolanoff | 424/258 |
| 4,424,215 | 1/1984 | Buerstinghaus et al. | 424/210 |
| 4,424,217 | 1/1984 | Reifschneider | 424/216 |
| 4,425,361 | 1/1984 | Lohmann et al. | 424/309 |
| 4,427,700 | 1/1984 | Retnakaran | 424/324 |

OTHER PUBLICATIONS

Merck, 9th ed., "Iridomyrmecin"; Abstract 4938, p. 669 (1976).
Merck, 9th ed. "Baygon", Abstract 7625, p. 1015 (1976).
CA 41:3575h (1946) (Eddy et al.).
*Tetrahedron*, 1959, vol. 6, pp. 201–216, by F. Korte et al.

*Primary Examiner*—Albert T. Meyers
*Assistant Examiner*—F. Krosnick
*Attorney, Agent, or Firm*—Leydig, Voit & Mayer

[57] ABSTRACT

Compositions containing certain bicyclic lactones and having insect repellent properties are disclosed. Such compositions comprise a compound of the formula:

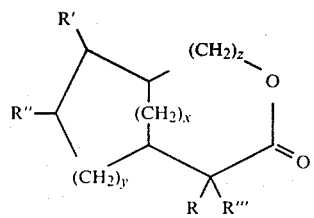

or the corresponding unsaturated compound thereof having the formula:

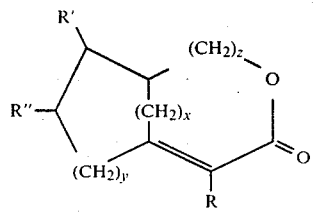

wherein R, R', R" and R'" each are lower alkyl or hydrogen; wherein y is an integer from 1–3, and x and z each are 0 or 1, with the proviso that y is 1 or 2 when x is 1; and a carrier. A method of using such a repellent composition to repel an insect from a situs comprises applying to such situs an effective amount of the composition, with or without the carrier, and thereby repelling the insect from the situs.

4 Claims, No Drawings

INSECT REPELLENT

BACKGROUND OF THE INVENTION

The present invention is directed to a class of bicyclic lactones useful as insect repellents.

The search for insect repellent compounds characterized by a combination of excellent repellency, high residual activity and relatively little or no toxicity to humans is a continuing one due to recognition of possible toxicity to humans (or pets). Thus, relatively long-lasting repellent compounds, having essentially no toxic effects upon humans, are currently in great demand.

REPELLENTS: AS DISTINGUISHED FROM INSECTICIDES

Repellent substances are known to cause insects to be driven away from or to reject (otherwise insect-acceptable) food sources. Most known repellents are only mildly toxic. A few of the known repellents, in fact, are not active poisons at all; but rather, prevent damage to plants or animals by making insect food sources or living conditions unattractive or offensive.

Repellents may be in the form of gases (olfactory), liquids, or solids (gustatory). Some well-known insect repellents include: benzil; benzyl benzoate; 2,3,4,5-bis(-butyl-2-ene) tetrahydrofurfural (MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (also known as Delphone, Detamide, Autan, or, more simply, Deet); dimethyl carbate (cis-bicyclo-[2.2.1]-5-heptene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; and normal-propyl N, N-diethylsuccinamate. Standard repellents for mosquitoes, ticks, and the like are citronella oil, dimethyl phthalate, normal-butylmesityl oxide oxalate and 2-ethyl hexanediol-1,3. See Kirk-Othmer *Encyclopedia of Chemical Technology*, Second Edition, Volume 11, pps. 724–728; and *The Condensed Chemical Dictionary*, Eighth Edition, Page 756.

Cost considerations, moreover, often become important when choosing an effective repellent. A number of the above-mentioned repellents are only effective in relatively concentrated form. Commercially available repellent products, which may include Deet as the active repellent ingredient thereof, may include as much as 5-30% (or more) repellent in a carrier, based on total weight. U.S. Pat. No. 4,416,881 to McGovern et al., for example, discloses repellent concentrations of 6.25-25% repellent in a carrier. U.S. Pat. No. 4,419,360 to Smolanoff, in its test examples, discloses repellent concentrations of 5% repellent in a carrier.

Insecticides function by poisoning via oral ingestion of stomach (or other organ) poisons, by contact with the insect cuticle, or by fumigant action through the air. As is well known, the term "insect" refers to any member of a large group of invertebrate animals characterized, in the adult state (non-adult insect states include larva and pupa), by division of the body into head, thorax, and abdomen, three pairs of legs, and, often but not always, two pairs of membranous wings, viz., the dictionary definition of insects, in addition to including beetles, bees, flies, wasps, mosquitoes, etc., also includes wood lice, mites, ticks, and the like.

As is well known, an insecticide is a type of pesticide designed to control insect life which is harmful to man. Such harm can be manifested either directly as disease vectors, or indirectly as destroyers of crops, food products, or textile fabrics. Several well-known insecticides include: inorganic compounds (such as arsenic, lead and copper); naturally occurring organic compounds (such as rotenone, pyrethrins, nicotine, copper naphthenate and petroleum derivatives); and synthetic organic compounds (such as DDT, dieldrin, endrin, chlordane, lindane, para-dichlorobenzene and parathion).

Another group of organic insecticides acts on the principle of metabolic inhibition and, accordingly, are known as antimetabolites. Besides direct application onto a plant so as to be directly contactable by an insect (e.g., an insect larva), certain antimetabolites can be fed to growing plants either as a nutrient or a non-nutritional ingredient therefor with the result being that such a host plant will incorporate the antimetabolite into its plant tissue and, upon transfer of the antimetabolite into the insect via ingestion, no longer serve as a food source for the insect. See Kirk-Othmer *Encyclopedia of Chemical Technology*, 2nd Edition, published by John Wiley & Sons, Inc., Volume 11, pps. 677–738 (1966); and *The Condensed Chemical Dictionary*, 8th Edition, Published by Van Nostrand Reinhold Company, Pages 469–470 (1971).

Accordingly, it is generally well known that most insecticides are toxic to man in varying degrees.

PRIOR ART

In 1959, several investigators (viz., F. Korte, J. Falbe and A. Zschocke) of the Chemical Institute at Bonn University, West Germany, reported (in *Tetrahedron*, 1959, Volume 6, pp. 201–216) a number of generally applicable methods for synthesizing a variety of bicyclic gamma- and delta-lactones, including the method for synthesizing D,L-Iridomyrmecin. In the Korte article, it was noted that some of the therein-disclosed compounds exhibited insecticidal properties. (One of the investigators, Korte, it will be noted, is a named coinventor herein.) It was only recently (1982), however, that the insecticidal properties of Iridomyrmecin and a number of the other bicyclic lactones discussed in the article were studied in somewhat greater detail by us.

A brief investigation of the current insect repellent art has revealed no lactone-based substances which function as insect repellents. See, e.g., U.S. Pat. Nos. 4,419,360 to Smolanoff and 4,416,881 to McGovern et al.

Indeed, in light of the above-presented discussion directed to the different principles of operation between insecticides and repellents, it is not at all obvious that a substance having insecticidal properties would also have repellent properties.

Moreover, for an insecticide to be effective, it is generally thought that such ought not have any repellent activity (or characteristics) whatsoever. Otherwise, a pest would never make contact with the insecticide, and the insecticide would therefore not achieve its intended purpose. Accordingly, a number of insecticides are manufactured to include means for attracting pests: a few commercially available insecticides, e.g., include well-known pest attractants which serve to attract a pest and induce it to come into contact with the insecticide. See Kirk-Othmer *Encyclopedia of Chemical Technology*, Second Edition, Volume 11, pp. 729-731.

As will be recalled, a lactone is an inner ester of a carboxylic acid formed by intramolecular reaction of hydroxylated or halogenated carboxylic acids with elimination of water and/or hydrogen chloride. In other words, a lactone is a cyclic ester. For example, well-known gamma- and delta-lactone compounds can be made via classical mechanisms respectively represented below by equations (1) and (2).

I.e., gamma- and delta-carboxylic acids (preferably respectively gamma- and delta-hydroxy acid salts thereof) can be esterified via well-known mechanisms for producing the respective 5- and 6-membered lactone rings presented below.

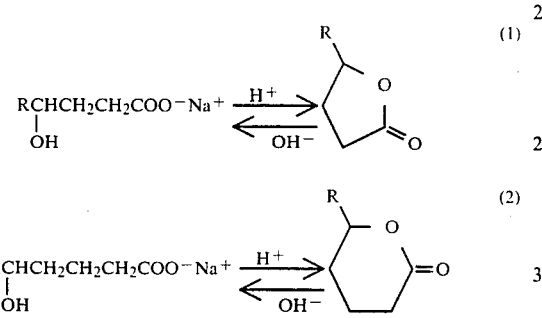

wherein R can be selected, e.g., from the group consisting of hydrogen, methyl, ethyl, propyl and butyl (i.e., lower alkyl). See, *The Condensed Chemical Dictionary*, 8th Edition, p. 502; and *Organic Chemistry*, Second Edition, by R. T. Morrison and R. N. Boyd, published by Allyn and Bacon, Incorporated, p. 953 (1966).

OBJECTS AND SUMMARY OF THE INVENTION

It is therefore a general object of this invention to provide compositions having improved insect repellent activity.

A more specific object is to provide bicyclic lactone compositions having such repellent properties.

A related object is to provide insect repellent bicyclic lactone compositions which are substantially non-toxic or only mildly toxic to humans.

Yet another object is to provide bicyclic lactones which, when included in relatively minor amounts in an inert carrier, possess effective insect-repelling properties.

A related object is to provide a relatively-inexpensive insect-repellent composition which preferably includes relatively minor amounts of repellent in a carrier.

A further object is to provide methods of repelling insects using such bicyclic lactones.

In accordance with the foregoing objects, bicyclic lactone compositions having insect repellent properties will now be summarized. Such a repellent comprises a compound of the formula:

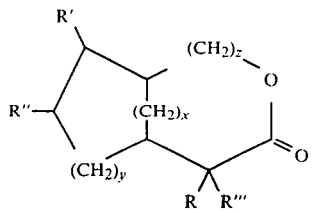

or the corresponding unsaturated compound thereof having the formula:

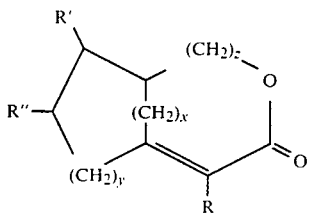

wherein R, R', R" and R''' each are lower alkyl (e.g., C1-C4) or hydrogen; wherein y is an integer from 1-3, and x and z each are 0 or 1, with the proviso that y is 1 or 2 when x is 1; and a carrier. Preferably, R, R', R" and R''' each are hydrogen or methyl.

The foregoing, as well as other objects, features and advantages of the present invention, will become more readily understood upon reading the following detailed description.

DETAILED DESCRIPTION OF THE PREFERRED COMPOUNDS

Values of structural variables of the preferred bicyclic lactones, and abbreviations used throughout this application to refer to such lactones, appear below in Table I:

TABLE I

| Abbreviation | Compound is | Values of Structural Variables | | | | | | |
|---|---|---|---|---|---|---|---|---|
| | | x | y | z | R | R' | R" | R''' |
| CIC-2 | sat. | 0 | 1 | 1 | $CH_3$ | $CH_3$ | H | H |
| CIC-3a | sat. | 0 | 2 | 1 | $CH_3$ | H | H | H |
| CIC-4 | sat. | 0 | 2 | 1 | H | H | H | H |
| CIC-5 | unsat. | 0 | 2 | 1 | $CH_3$ | H | H | non. |
| CIC-6 | sat. | 0 | 1 | 1 | H | H | H | H |
| CIC-7 | unsat. | 0 | 2 | 1 | H | H | H | non. |
| CIC-8 | sat. | 0 | 1 | 1 | $CH_3$ | H | H | H |
| CIC-9 | unsat. | 0 | 1 | 1 | H | H | H | non. |
| CIC-10 | unsat. | 0 | 1 | 1 | $CH_3$ | H | H | non. |
| CIC-20 | sat. | 0 | 2 | 0 | $CH_3$ | H | H | H |
| CIC-21 | sat. | 0 | 2 | 0 | $CH_3$ | $CH_3$ | H | H |
| CIC-23 | sat. | 1 | 1 | 0 | $CH_3$ | H | H | H |
| CIC-24 | sat. | 1 | 1 | 0 | $CH_3$ | H | $CH_3$ | H |
| CIC-25 | sat. | 1 | 1 | 0 | $CH_3$ | $CH_3$ | H | H |
| CIC-26 | sat. | 0 | 3 | 1 | $CH_3$ | H | H | $CH_3$ | sat. = saturated
non. = nonexistent
unsat. = unsaturated

Somewhat more widely-recognizable names for these compounds are as follows. CIC-2 is known as alpha-(2-hydroxymethyl-3-methyl-cyclopentyl) propionic acid lactone. Its trivial name is Iridomyrmecin. CIC-3a is known as alpha-(2-hydroxymethyl-cyclohexyl) propionic acid lactone. CIC-4 is known as (2-hydroxymethyl-cyclohexyl) acetic acid lactone. CIC-5 is known as alpha-(2-hydroxymethyl-cyclohexylidene) propionic acid lactone. CIC-6 is known as (2-hydroxymethylcyclopentyl) acetic acid lactone. CIC-7 is known as (2-hydroxymethyl-cyclohexylidene) acetic acid lactone (see, B. Belleau, *Canadian Journal of Chemistry*, 35, 673 (1957)). CIC-8 is known as alpha-(2-hydroxymethyl-cyclopentyl) propionic acid lactone. CIC-9 is known as (2-hydroxymethyl-cyclopentylidene) acetic acid lactone. CIC-10 is known as alpha-(2-hydroxymethyl-cyclopentylidene) propionic acid lactone. CIC-20 is known as alpha-(2hydroxycyclohexyl) propionic acid lactone. CIC-21 is known as alpha-(2-hydroxy-4-methylcyclohexyl) propionic acid lactone. CIC-22 is known as alpha-(2-hydroxy-3-methylcyclohexyl) propionic acid lactone. CIC-23 is known as alpha-(3-hydroxy-cyclohexyl) propionic acid lactone. CIC-24 is known as alpha-(3-hydroxy-4-methylcyclohexyl) propionic acid lactone. CIC-26 is known as alpha-(2-hydroxycycloheptyl) alpha, alphadimethyl propionic acid lactone.

The class of bicyclic lactones shown in Table I was recently discovered by us to be an effective non-contact insect repellent, viz., the insect is repelled, usually without having made contact with the repellent or host.

The nomenclature used in this patent has been used in the literature (including the *Tetrahedron* article referred to above) and throughout the Chemical Abstracts up to 1966. After 1967, the Chemical Abstracts generally have used and now use the following names for the underlying CIC chemical skeletal structure, with the noted exception.

| CHEMICAL SKELETAL STRUCTURE | CHEMICAL ABSTRACTS NAME |
|---|---|
| | 5,6,7,7a-Tetrahydrocyclopenta[c] pyran-3 (1H)—one |
| | Hexahydrocyclopenta[c] pyran-3 (1H)—one |
| | 1,5,6,7,8,8a-Hexahydro-3H—2-benzopyran-3-one |
| | Hexahydro-3-isochromanone (up to 1972), (and after 1972) 1,1,4,5,6,7,8,8a-Octahydro-3H—2-benzo-pyran-3-one |
| | Hexahydro-2(3H)—benzofuranone |
| | 2-Oxabicyclo [3.3.1] nonan-3-one |
| | Hexahydrocyclohepta[c] pyran-3(1H)—one |

METHODS OF USE

A method of using the above-disclosed lactone compounds to repel an insect from a situs comprises applying to such situs an effective amount of the lactone compound for thereby repelling the insect from the situs. Preferably, the lactone compound is used in combination with a carrier. Some carriers, it will be noted, can themselves have repellent properties.

The term "situs", as it is used throughout this application, will be understood to mean a position or location on specified plant or animal cells (or tissue), including a position or location proximate or adjacent thereto.

The lactone repellent compositions of the present invention thus can be formulated without a carrier or they can include suitable carriers for bringing the active material into position for repelling common insect pests such as roaches, moths, house and stable flies, termites, flour beetles, bean beetles, weevils, ticks, chinch bugs, lice, ants, chiggers, mosquitoes, and the like.

Insects can be repelled by contacting the surfaces on which such insects may alight or crawl with a liquid, solid, or semi-solid composition. Such contact can be accomplished directly, e.g., by dispersing the composition into the air, as a liquid mist or fine dust, in a manner such that the composition will fall on desired surfaces.

By way of further example, insect-infested animals, such as dogs with fleas, poultry with lice, cows with ticks, or monkeys (and other primates such as humans) with mosquitoes, can be treated with the insect repellent compound of the present invention, by contacting the skin, fur or feathers of such an animal with an effective amount of the repellent compound for repelling the insect from the animal. (More specific examples will be discussed below in connection with the "tests".)

By way of yet further example, granaries and grain storage facilities such as silos can be treated with relatively minute effective amounts of the repellent compositions (of the present invention), preferably prior to grain storage, to prevent beetle, weevil, and other insect infestations, otherwise present in the grain, thereby permitting such grain satisfactorily to be stored without fear of insect destruction.

In addition, food-packaging containers, including fiber, cardboard, and wooden shipping containers, storage bins, flour sacks, and the like, can be treated with relatively minute effective amounts of the repellent composition (of the present invention) to prevent insect infestation.

METHOD OF MAKING A LACTONE

CIC-2, Iridomyrmecin, was in 1959 reported as having been synthesized in 1958, and the synthesis thereof is reported in the chemical literature. See, *The Merck Index*, Ninth Edition, Published by Merck & Company, Inc., p. 669, No. 4938 (1976); and Korte et al., *Tetrahedron*, 6, 201 (1959), noted above. In the *Tetrahedron* article, which we incorporate by reference, the methods of producing the CIC-3a, CIC-4, CIC-5, CIC-6, CIC-8, CIC-10 and CIC-26 compounds are also reported. We now briefly present, hereinbelow, our reported method of manufacturing or synthesizing CIC-2.

A first chemical, referred to as alpha-(1-hydroxy-3-methylcyclopentyl) ethyl propionate was made as follows: 120 grams of bromopropionic acid ethyl ester, 43 grams of 3-methyl-cyclopentanone-1 and five grams of zinc shavings were combined with 300 milliliters of anhydrous benzene in a vessel, and were therein stirred and heated to 80° C. Upon initiation of reaction, the heat source was removed. In due course (i.e., 45 minutes) an additional quantity (35 grams) of zinc was added, in portions to the vessel, whereupon violent reaction was observed. The reactants were refluxed for three hours. After being refluxed and upon being cooled, the reactants were acidified to appropriate pH with 20% $H_2SO_4$. Thereafter, the benzene layer and aqueous phase were separated, and the aqueous phase was extracted several times with benzene. The various benzene solutions were combined, dried over calcium chloride, and the benzene removed from the solution via vacuum distillation. Distillation conditions were 30 millimeters of mercury (absolute pressure), resulting in a boiling point (b.p.) of 122°-124° C. and a yield of 68 grams (84% of the theoretical yield) of this first chemical.

Next, a first intermediate chemical mixture, referred to as an isomeric mixture consisting of alpha-(3-methyl-cyclopenten-1-yl)-ethyl propionate, alpha-(4-methyl-cyclopenten-1-yl)-ethyl propionate, and alpha-(3-methyl-cyclopentylidene)-ethyl propionate was synthesized as follows: 65 grams of the above-described first chemical, 18 grams of $POCl_3$ and 150 milliliters of anhydrous benzene were combined and refluxed until termination of evolution of HCl (4 hours). After refluxing and upon being cooled, benzene solution was extracted with ice water and ice-cold sodium bicarbonate solution, and the extracted benzene solution thereafter dried over calcium chloride. Vacuum distillation, similar to that described above for isolation of the first chemical, was employed with the result being that a colorless oil was obtained, the oil having a b.p. (at 8 millimeters of mercury absolute pressure) of 97°-99° C., weighing 54 grams (a yield of 91% of the theoretical yield), such oil being the first intermediate chemical mixture described above.

Next, a second intermediate chemical mixture, chemically referred to as an isomeric mixture comprising alpha-(3-methyl-cyclopenten-1-yl)-propionic acid and alpha-(4-methyl-cyclopenten-1-yl)propionic acid, was synthesized as follows: 51 grams of the first intermediate chemical mixture, 120 milliliters of ethanol and 30 milliliters of 50% KOH were combined and refluxed for six hours. After refluxing and upon being cooled, the reaction mixture was poured into one liter of water whereupon extraction, using ethyl ether, was undertaken to remove impurities from the reaction mixture. The ether layer was discarded. The aqueous phase was acidified with 20% HCl, and extracted several times with fresh ether. The ether extract solutions were combined, dried over magnesium sulfate, and the ether removed therefrom via vacuum distillation. UV (ultraviolet) spectra disclosed that the chemical compounds of the second intermediate chemical mixture could quantitatively be separated via fractional distillation. Accordingly, a first fraction formed a colorless oil having a b.p. (at 0.02 millimeters of mercury absolute pressure) of 70°-71° C., resulting in a yield of 26 grams (60.5% of the theoretically yield) thereof. The first fraction was a mixture of alpha-(3-methylcyclopenten-1-yl) propionic acid and alpha-(4-methylcyclopenten-1-yl) propionic acid. A second fraction appeared as crystals having a m.p. (melting point) of 56° C. and a b.p. (at 0.02 millimeters of mercury absolute pressure) of 75°-77° C., resulting in a yield of 14 grams (32.6% of the theoretical yield) thereof. The second fraction was alpha-(3-methylcyclopentylidene) propionic acid.

A third intermediate chemical mixture, chemically referred to as an isomeric mixture comprising alpha-(3-methyl-2-hydroxymethylcyclopentylidene)-propiolactone and alpha-(4-ethyl-2-hydroxymethyl-cyclopentylidene)-propiolactone, was synthesized as follows: 23 grams of the first fraction described in the preceding paragraph, 6.5 grams of paraformaldehyde and 80 milliliters of glacial acetic acid/sulfuric acid (100:1.5) were combined and refluxed for six hours. After refluxing and upon being cooled, 5 grams of sodium acetate were added thereto, and the solvent removed therefrom via vacuum distillation, resulting in a residue. The residue was combined with ethyl ether, then washed first with ice-cold aqueous sodium carbonate solution and subsequently with water. After being dried over $MgSO_4$, the ether was removed via vacuum distillation, resulting in a colorless oil having a b.p. (at 0.02 millimeters of mercury absolute pressure) of 70° C., and a yield of 17 grams (69% of the theoretical yield) thereof.

Iridomyrmecin, more specifically a racemic mixture of D, L-Iridomyrmecin, was then accordingly synthesized as follows: 9 grams of the third intermediate chemical mixture, three grams of Raney-nickel and 500 milliliters of ethanol solvent were combined and thereafter transferred into a stirred autoclave and therein hydrogenated at 100° C. and 100 atmospheres (of hydrogen pressure) until a constant pressure was achieved in the autoclave (2 hours). Thereafter, the Raney-nickel was removed from the mixture by filtration, and the ethanol solvent was subsequently removed therefrom. The distillation product, which included Iridomyrmecin, was obtained by distillation at 82° C. at 0.3 millimeters of mercury absolute pressure in a yield of 7.5 grams (83% of the theoretical yield). The Iridomyrmecin was thereafter crystallized out of the distillation product.

This method, moreover, was recently used by us to synthesize the above-disclosed CIC-7, CIC-9 and, with a modification, the CIC-20 through CIC-24 compounds (which had not been reported in the *Tetrahedron* article). The modification used in the synthesis of the CIC-20 through CIC-24 compounds is an intramolecular addition of the carboxylic acid moiety to the olefinic double bonds in the corresponding alpha-(cyclohexen-1-yl)-propionic acids, instead of the "Prins" reaction with paraformaldehyde (step 3) and hydrogenation (step 4) following, as described above. This type of reaction, which includes chemical skeletal structure partial rearrangement (depending on the reaction conditions), is an established procedure described by H. Wamhoff in *Methodicum Chemicum*, Vol. 5, p. 689, Georg Thieme Verlag, Stuttgart/West Germany 1975 and H. Kroper in Houben-Weyl, *Methoden der Organischen Chemie*, 4th ed., Vol. VI/2, p. 561, Georg Thieme Verlag, Stuttgart/West Germany 1963, and the references cited therein.

CARRIERS

In the present invention, a variety of carriers (or diluents) for the above-disclosed bicyclic lactones can be used.

The amount of lactone compound included in the repellent composition can vary from about 0.00001–100 weight percent, based upon the total weight of the insect repellent composition, and will depend upon the intended use. In other words, the repellent compositions of the present invention can exclude the carrier and be effective. More often, however, the insect repellent composition will include a carrier and contain about 0.00001–10 weight percent of the above-disclosed lactone compound, and such compound is usually in intimate mixture with the carrier. Preferably, the composition will contain about 0.001–1.5%, by weight, of the above-disclosed bicyclic lactone compound in a carrier.

The carrier used can be any carrier conventionally used in insect repellent formulations. The carrier, moreover, should preferably also be one that will not be harmful to the environment.

Accordingly, the carrier can be any one of a variety of commercially available organic and inorganic liquid, solid, or semi-solid carriers or carrier formulations usable in formulating insect repellent products.

Examples of organic liquid carriers include liquid aliphatic hydrocarbons such as pentane, hexane, heptane, nonane, decane and their analogs, as well as liquid aromatic hydrocarbons. Examples of other liquid hydrocarbons include oils produced by the distillation of coal and the distillation of various types and grades of petrochemical stocks, including kerosene oils which are obtained by fractional distillation of petroleum.

Other petroleum oils include those generally referred to (in the art) as agricultural spray oils, the so-called light and medium spray oils, consisting of middle fractions in the distillation of petroleum, and which are only slightly volatile. Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used.

Other organic liquid carriers can include liquid terpene hydrocarbons and terpene alcohols such as alpha-pinene, dipentene, terpineol, and the like.

In addition to the above-mentioned liquid hydrocarbons, the carrier can contain conventional emulsifying agents which can be used for causing the lactone compounds to be dispersed in, and diluted with, water for end-use application.

Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable dihydric alcohols include glycols (such as ethylene and propylene glycol) and the pinacols (alcohols having the empirical formula $C_6H_{12}(OH)_2$). Suitable polyhydroxy alcohols include glycerol, arabitol, erythritol, sorbitol, and the like. Suitable cyclic alcohols include cyclopentyl and cyclohexyl alcohols.

Conventional aromatic and aliphatic esters, aldehydes and ketones can be used as carriers, and occasionally are used in combination with the above-mentioned alcohols.

Still other liquid carriers include relatively high-boiling petroleum products such as mineral oil, and higher alcohols (such as cetyl alcohol) can similarly be used.

Additionally, conventional or so-called "stabilizers", such as tert-butyl sulfinyl dimethyl dithiocarbonate, can be used in conjunction with, or as a component of, the carrier or carriers comprising the composition of the present invention.

Solid carriers which can be used in the compositions of the present invention include finely divided organic and inorganic solid materials. Suitable finely divided solid inorganic carriers include siliceous minerals such as clay, bentonite, attapulgite, fuller's earth, diatomaceous earth, kaolin, mica, talc, finely divided quartz, and the like, as well as synthetically prepared siliceous materials, such as silica aerogels and precipitated and fume silicas.

Examples of finely divided solid organic materials include cellulose, sawdust, synthetic organic polymers, and the like.

Examples of semi-solid or colloidal carriers include waxy solids, gels (such as petroleum jelly), lanolin, and the like, and mixtures of well-known liquid and solid substances which can provide semi-solid carrier products, for providing effective repellency within the scope of the instant invention.

REPELLENT ACTIVITY

As briefly mentioned above, the CIC-2 compound was recently (1982) discovered to have effective insecticidal properties at concentrations of as little as 0.00001–1.5%, by weight, bicyclic lactone in carrier.

More importantly, however, and also quite unexpectedly, we have discovered the present invention: that the CIC-2 compound is also a potent repellent. We have further discovered that a number of the bicyclic lactone compounds, reported in the *Tetrahedron* article, also exhibit insect repellent activity.

TESTS

The repellent activity of the CIC-2 compound against *Solenopsis invicta* (the imported Fire Ant), on a comparative basis, as measured against three commercially-available repellents, is presented below in Table II.

TABLE II

| Compound | Repellent Activity Scale[1] (1–10) |
|---|---|
| CIC-2 | 9 |
| Baygon[2] | 8 |
| Oftanol[3] | 4 |
| Volaton[3] | 2 |

[1]Repellent activity was based on a 1–10 scale where 1 represents substantially no noticeable repellent activity and 10 represents substantially complete (or full-strength) repellent activity. Tests involved testing repellent activity of noted repellent against about 15–30 worker caste Fire Ants per petri dish.
[2]BAYGON, a commercially-available insecticide, is the trademark for 2-(1-Methylethoxy)phenol methylcarbamate. (See The Merck Index, 9th Ed., No. 7625, p. 1015.)
[3]Commercially available repellents.

The comparative repellency, as between the CIC-2 compound and a well known product (Deet), is presented below in Table III.

TABLE III

| Chemical | Total %[4] | mg/cm²[5] | Time of Activity (hours:minutes) | Remarks |
|---|---|---|---|---|
| CIC-2 | 0.50 | 0.132 | 3:00 | 15/26 bit |
| Deet[6] | 0.50 | 0.132 | 3:00 | 4/27 bit |

[4]Total percentage, by weight, of chemical in solution of carrier. Carrier solutions comprised 95% ethanol.
[5]Approximate quantity of noted repellent compound per monkey-skin surface area.
[6]N,N—diethyl-meta-toluamide. (See, The Merck Index, 9th Ed., No. 3118, p. 415.)

The repellencies of the CIC-2 compound and Deet were comparatively tested upon rhesus monkeys against mosquitoes (*Aedes aeqypti*), and we noted how many mosquitoes bit a particular monkey which had the above-identified repellent compound topically applied.

Additional tests noting the repellency of the CIC-2, CIC-3a, CIC-4 through CIC-10, and CIC-20 through CIC-22 compounds, in connection with the rhesus monkey, appear below in Table IV.

TABLE IV

| Chemical | %[7] | Mg/cm²[8] | Time of Activity (hours:minutes) | Remarks |
|---|---|---|---|---|
| CIC-2 | 1% | 0.263 | >5:30 | Experiment stopped after 5.5 hours; no bites. |
| CIC-2 | 1% | 0.263 | 6:00 | 12/24 mosquitoes bit after 6 hours. |
| CIC-3a | 1% | 0.263 | >10:25 | Terminated before mosquitoes bit. |
| CIC-4 | 1% | 0.263 | 4:30 | 7/16 mosquitoes bit. |
| CIC-5 | 1% | 0.263 | 4:30 | 4 mosquitoes bit; but repellency otherwise satisfactory. |
| CIC-6 | 1% | 0.263 | 2:00 | 14/24 bit after 2 hrs. |
| CIC-7 | 1% | 0.263 | 4:00 | 8/40 bit; chemical had different odor than CIC-2, like valeric acid. Stunned mosqs. |
| CIC-8 | 1% | 0.263 | 4:00 | 25/28 bit after 4 hrs. |
| CIC-9 | 1% | 0.263 | 4:00 | 10/25 bit; chemical was thick and waxy. |
| CIC-10 | 1% | 0.263 | 5:00 | 8/28 bit; chemical thick. |
| CIC-20 | 1% | 0.263 | 1:30 | 8/23 bit, and then terminated. |
| CIC-21 | 1% | 0.263 | 2:40 | 7/18 bit, and then terminated. |
| CIC-22 | 1% | 0.263 | 2:40 | 16/33 bit, and then terminated. |

[7]Percentage of bicyclic lactone repellent, by weight, in solvent carrier. Solvent carrier comprised 95% ethanol.
[8]Concentration of bicyclic lactone repellent on monkey skin. Approximately 4 sq. in. of monkey stomach skin surface was tested.

In addition, the repellent activity of the above-presented lactones was tested upon flies and fleas.

Briefly summarizing experimental findings (not all of which are specifically tabulated herein):

The CIC-2 compound at 1% (in 95% ethanol) was observed to be a potent repellent when tested against fire ants, mosquitoes, fleas, and flies.

The CIC-3a compound was observed to be a potent repellent, for guinea pigs, against *Aedes aegypti*, the skin of the guinea pigs having been treated with the compound CIC-3a in a carrier.

The insect repellent activities of the compounds CIC-4, CIC-20 and CIC-23 were observed (in certain experiments) to be just as effective as, or better than, the CIC-2 and CIC-3 a compounds.

These findings as well as other observations by us will be explained in greater detail in the "testing procedures" section appearing immediately below.

TESTING PROCEDURES

The experimental procedures for the above-disclosed tests can be briefly summarized as follows. Filter paper was wetted with a carrier solution of a particular bicyclic lactone dissolved either in 50% acetone in water or in 95% ethanol. After the filter paper was dried, it was placed in a standard petri dish. A variety of insects, including Fire Ants, mosquitoes, flies, and fleas, were tested by being separately placed on filter paper in respective petri dishes, with and without the bicyclic lactone being present on certain ones of these filter paper test sites. All tests were respectively performed against approximately 15–30 worker-caste type Fire Ants, several hundred mosquitoes, about 15 stable flies and approximately 20 oriental rat fleas. Most of the experiments were done in triplicate.

The concentration of each bicyclic lactone compound, if being tested in a carrier, ranged from about 0.001 to about 1.5% (by weight of chemical in carrier solvent) on the filter paper.

In other tests, a relatively small amount of each bicyclic lactone compound without a carrier was placed approximately in the center of a dry petri dish and Fire Ants were placed in the petri dish to observe whether or not the ants approached the chemical. In studies testing repellent activity of crystals of the CIC-2 compound (no carrier being present), Fire Ants avoided contact with these crystals and rapidly went to the periphery of the petri dish.

In yet other tests, measured amounts of the CIC-2 compound were dissolved either in 95% ethyl alcohol carrier or 50% acetone carrier and applied to human skin. After the ethanol or acetone-water carrier solvent evaporated, the CIC-2 was left on the skin. Gloves were then placed on the hand of the human subject being tested, and the hand and forearm placed in cages containing various single species of mosquitoes, including *Anopheles quadrimaculatus*, *Anopheles albimanus*, *Aedes aegypti* and *Culex Anopheles albimanus*, *Aedes aegypti* and *Culex salinarius*. The forearm of the human subject was allowed to remain in the cage with hundreds of mosquitoes for about three minutes with observation as to whether any of the female mosquitoes had bitten. The arm was then removed and, thirty minutes later, was reinserted into the cage for a period of three minutes. This process was repeated until more than six mosquitoes had bitten, which was considered the end point for each repellent activity determination test.

In still other tests, different species of mosquitoes, particularly *Culex nigripalpus*, were prepared in plastic globes each having an open end and containing approximately twenty-five females. Tests were performed by placing the open end of the globe, covered with mosquito netting, directly on the forearm of the human subject, with and without the compound CIC-2 being topically applied to the subject's forearm.

A limited number of similar experiments were also performed against the stable fly (*Stomoxys calcitrans*) and the oriental rat flea (*Xenopsylla cheopsis*).

Additional studies were made against fruit flies (Drosophila), comparing the repellent activity of about 1%, by weight, of the CIC-2 compound to about 30%, by weight, Deet in a carrier. The repellent activity of the CIC-2 compound, at these relative concentrations, was as good as or better than that of Deet. It was thus observed that relatively substantially less bicyclic lactone repellent (than Deet), in carrier, was sufficient for effecting substantially equivalent or better repellent activity against a variety of insects. In these comparisons, weight was based on weight % of the repellent compound in 95% ethanol carrier.

Yet another series of tests was performed against *Culex nigripalpus*, in which approximately 25 female mosquitoes (in globes) were placed on the arm of a human subject treated with the CIC-2 compound at the 1% (by weight) concentration, along with a control subject without such treatment. A strong repellent activity (for the treated subject) was observed, lasting for about four minutes; the control subject, however, was immediately bitten.

A further experiment was performed upon another human subject treated on one arm with 1.5 weight percent CIC-2 compound in 95% ethyl alcohol carrier, and on the other arm with 1 weight percent CIC-2 compound in 50% acetone carrier. Sufficient volume (about 1 ml.) of the respective 1.5% and 1% solutions was placed on the subject's forearms for spreading about 50 milligrams of the CIC-2 compound on each forearm. The ethanol solution carrier was placed on the left forearm and the acetone solution carrier on the right. Upon evaporation of the respective ethanol and acetone carrier solvents, the left and right forearms were each placed in a large cage, each cage containing several hundred female mosquitoes of each of the following species: *Aedes aegypti, Anopheles quadrimaculatus, Anopheles albimanus,* and *Culex salinarius.* After three minutes, the subject's arms were removed (from the cages) and a rest period of thirty minutes was provided. After the rest period, the subject's arms were again placed in the respective cages. This experiment included insertion and removal of the subject's arms six times, every thirty minutes, each such experiment lasting about 180 minutes.

The CIC-2 compound was observed to be an ffective repellent against *Anopheles albimanus* and *Anopheles quadrimaculatus* throughout the 180-minute series of experiments, described immediately above. *Culex salinarius* and *Aedes aegypti,* on the other hand, were observed to overcome the repellent activity of the CIC-2 compound after approximately 90 minutes.

Otherwise, no observed differences were noted as between 95% ethanol and 50% acetone carrier solvents for the CIC-2 compound.

Yet further tests were performed comparing 1%, by weight, CIC-3a to 20%, by weight, Deet (in the above-described carrier solvents). The tests were performed upon guinea pigs against a variety of insects, and the CIC-3a was observed to have a relatively greater repellent activity than the Deet, at these concentrations. Such repellency, moreover, persisted for at least six hours.

CIC-2 additionally demonstrated a good-to-strong repellent activity particularly against stable flies.

What has been described herein are bicyclic lactone repellents, and methods of use thereof. While the lactone repellents of the instant invention have been presented and described with reference to preferred embodiments, the invention is not limited thereto. On the contrary, alternatives, changes or modifications may become apparent to those skilled in the art upon reading the foregoing description. Accordingly, such alternatives, changes, and modifications are to be considered as forming a part of the instant invention insofar as they fall within the spirit and scope of the appended claims.

We claim:

1. A method of repelling insects from a situs comprising applying to said situs a composition comprising an effective amount to repel said insects of a compound of the formula:

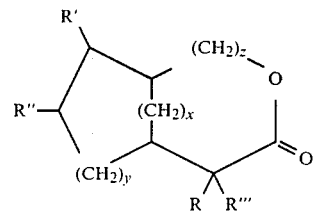

or the corresponding unsaturated compound thereof having the formula:

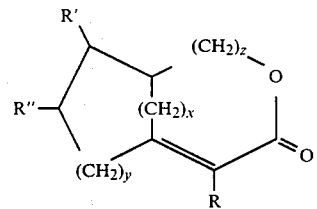

wherein R, R', and R" each are either methyl or hydrogen, and R''' is either hydrogen or methyl or is nonexistent; wherein y is an integer from 1–3, and x and z each are 0 or 1, with the proviso that y is 1 when x is 1.

2. The method of claim 1 wherein said composition further includes a carrier.

3. The method of claim 2 wherein said composition comprises about 0.001–1.5 weight percent of said compound in said carrier.

4. The method of claim 2, wherein said composition comprises from about 0.00001 to about 10.0 wt. % of said compound in said carrier.

* * * * *